United States Patent [19]

Jarsch et al.

[11] Patent Number: 5,229,286
[45] Date of Patent: Jul. 20, 1993

[54] CLONING AND OVEREXPRESSION OF GLUCOSE-6-PHOSPHATE DEHYDROGENASE FROM LEUCONOSTOC DEXTRANICUS

[75] Inventors: Michael Jarsch, Bad Heilbrunn; Gunter Lang, Tutzing, both of Fed. Rep. of Germany

[73] Assignee: Boehringer Mannheim GmbH, Mannheim-Waldhof, Fed. Rep. of Germany

[21] Appl. No.: 737,071

[22] Filed: Jul. 30, 1991

[30] Foreign Application Priority Data

Jul. 30, 1990 [DE] Fed. Rep. of Germany ....... 4024158

[51] Int. Cl.$^5$ ................................................ C12N 9/09
[52] U.S. Cl. ................................... 435/190; 530/350; 424/94.4; 435/14
[58] Field of Search ................ 424/94.4; 435/14, 188, 435/190

[56] References Cited

FOREIGN PATENT DOCUMENTS 2641285 12/1989 France .

OTHER PUBLICATIONS

Federation of European Biochemical Societies, vol. 211, No. 2, Jan. 1987, pp. 243–246, "Sequence identity between a lysine-containing peptide from Leuconostoc mesenteroides glucose-6-phosphate dehydrogenase and an active site peptide from human erythrocyte glucose-6-phosphate dehydrogenase", Bhadbhade, M. M. et al.

Journal of Bacteriology, vol. 169, No. 1, Jan. 1987, American Society for Microbiology, pp. 334–339, "Expression of the gene for NAD-dependent glucose-6-phosphate dehydrogenase from Leuconostoc mesenteroides cloned in Escherichia coli K-12", Murphy, N. B. et al.

Biochemical Society Transactions, vol. 17, No. 2, Apr. 1989, The Biochemical Society, London, GB, pp. 313–315, "Glucose-6-phosphate dehydrogenase from Leuconostoc mesenteroides", Levy, R. H.

Journal of Biological Chemistry, vol. 266, No. 20, Jul. 15, 1991, Baltimore, US, pp. 13028–13034, "Cloning of the gene and amino acid sequence for glucose-6-phosphate dehydrogenase from Leuconostoc mesenteroides", Lee, T. W. et al.

*Primary Examiner*—Robert A. Wax
*Assistant Examiner*—D. B. Schmickel
*Attorney, Agent, or Firm*—Nikaido, Marmelstein, Murray & Oram

[57] ABSTRACT

The invention concerns a glucose-6-phosphate dehydrogenase which contains the amino acid sequence shown in SEQ ID NO:1 as well as a DNA coding for it and a process for the isolation of an enzyme according to the present invention.

1 Claim, 1 Drawing Sheet

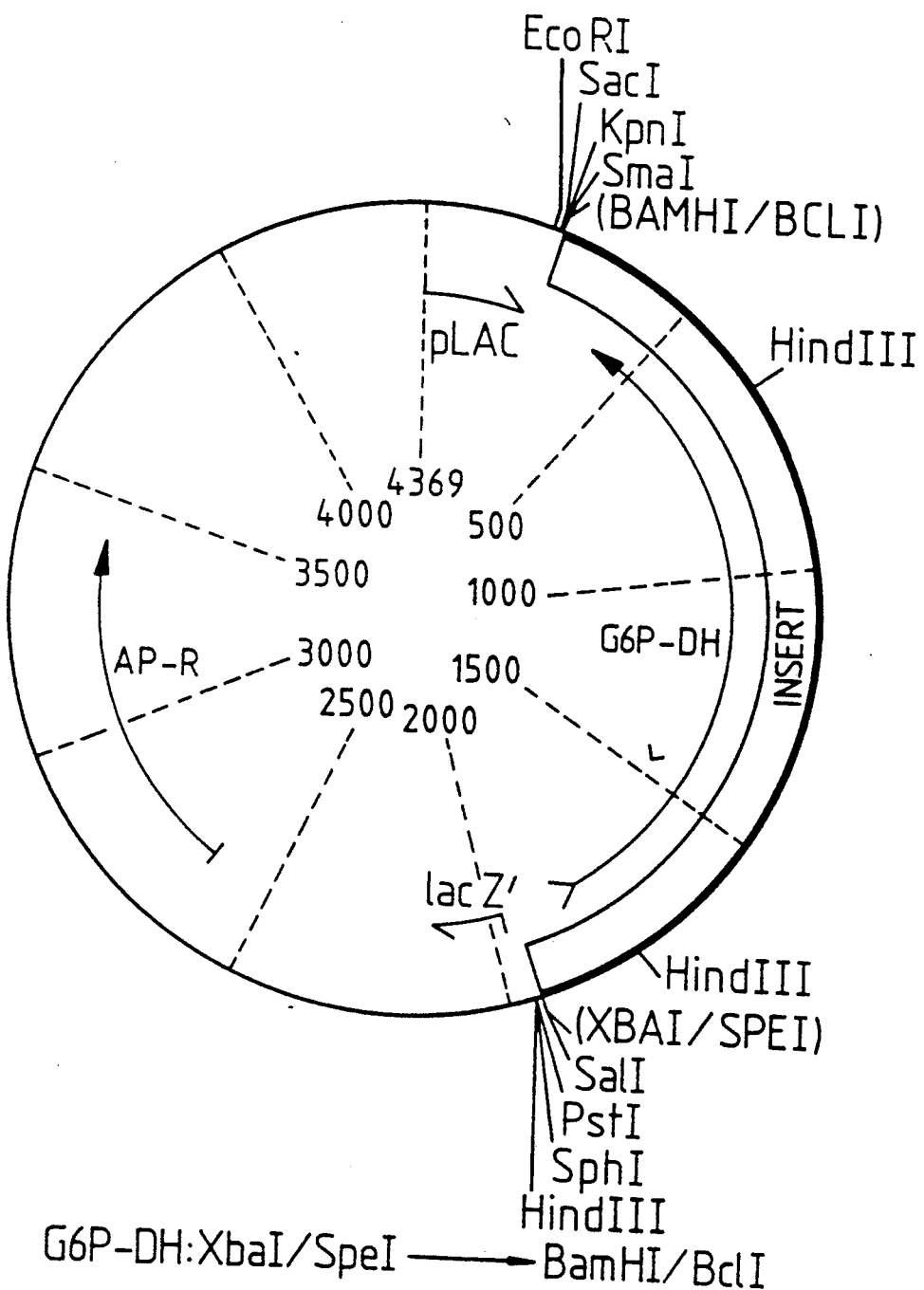

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1696 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 123..1580

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| TCTAGTCATT | TAATCAATTT | TTGACTTGTT | CAACGCTTAA | TATGTTTGTG | AATCCCGTAC | | | | | | | | | | | 60 |
| TTTTCCAGAC | CTTTTGCGT | TATAATGGAG | AGTGAATTTA | ATTATAATAT | AAGGGGAACA | | | | | | | | | | | 120 |

| TC | ATG | GTT | TCA | GAA | ATC | AAA | ACG | TTG | GTA | ACT | TTC | TTT | GGC | GGA | ACT | 167 |
|---|---|---|---|---|---|---|---|---|---|---|---|---|---|---|---|---|
| | Met | Val | Ser | Glu | Ile | Lys | Thr | Leu | Val | Thr | Phe | Phe | Gly | Gly | Thr | |
| | 1 | | | | 5 | | | | | 10 | | | | | 15 | |

| GGT | GAT | TTA | GCA | AAG | CGT | AAG | CTT | TAC | CCA | TCA | GTT | TTC | AAC | CTC | TAC | 215 |
|---|---|---|---|---|---|---|---|---|---|---|---|---|---|---|---|---|
| Gly | Asp | Leu | Ala | Lys | Arg | Lys | Leu | Tyr | Pro | Ser | Val | Phe | Asn | Leu | Tyr | |
| | | | 20 | | | | | 25 | | | | | 30 | | | |

| AAA | AAA | GGA | TAC | TTA | CAA | GAA | CAC | TTT | GCC | ATT | GTT | GGG | ACA | GCA | CGT | 263 |
|---|---|---|---|---|---|---|---|---|---|---|---|---|---|---|---|---|
| Lys | Lys | Gly | Tyr | Leu | Gln | Glu | His | Phe | Ala | Ile | Val | Gly | Thr | Ala | Arg | |
| | | | 35 | | | | | 40 | | | | | 45 | | | |

| CAA | CAA | TTA | AGT | GAT | GAC | GAG | TTT | AAG | CAA | TTG | GTT | CGT | GAT | TCA | ATT | 311 |
|---|---|---|---|---|---|---|---|---|---|---|---|---|---|---|---|---|
| Gln | Gln | Leu | Ser | Asp | Asp | Glu | Phe | Lys | Gln | Leu | Val | Arg | Asp | Ser | Ile | |
| | | 50 | | | | | 55 | | | | | 60 | | | | |

| AAA | GAC | TTT | ACT | GAA | GAT | CAA | GCA | CAA | GCC | GAA | GCG | TTT | ATT | GCG | CAT | 359 |
|---|---|---|---|---|---|---|---|---|---|---|---|---|---|---|---|---|
| Lys | Asp | Phe | Thr | Glu | Asp | Gln | Ala | Gln | Ala | Glu | Ala | Phe | Ile | Ala | His | |
| 65 | | | | | 70 | | | | | 75 | | | | | | |

| TTT | TCT | TAC | CGT | GCG | CAC | GAT | GTC | ACA | GAT | GCC | GCT | TCT | TAT | GGT | ATC | 407 |
|---|---|---|---|---|---|---|---|---|---|---|---|---|---|---|---|---|
| Phe | Ser | Tyr | Arg | Ala | His | Asp | Val | Thr | Asp | Ala | Ala | Ser | Tyr | Gly | Ile | |
| 80 | | | | | 85 | | | | | 90 | | | | | 95 | |

| TTG | AAG | TCA | GCG | ATC | GAA | GAA | GCA | GCA | ACC | AAA | TTT | GAC | ATT | GAT | GGC | 455 |
|---|---|---|---|---|---|---|---|---|---|---|---|---|---|---|---|---|
| Leu | Lys | Ser | Ala | Ile | Glu | Glu | Ala | Ala | Thr | Lys | Phe | Asp | Ile | Asp | Gly | |
| | | | | 100 | | | | | 105 | | | | | 110 | | |

| AAT | CGT | ATT | TTC | TAT | ATG | TCA | GTT | GCC | CCT | CGT | TTC | TTC | GGT | ACA | ATC | 503 |
|---|---|---|---|---|---|---|---|---|---|---|---|---|---|---|---|---|
| Asn | Arg | Ile | Phe | Tyr | Met | Ser | Val | Ala | Pro | Arg | Phe | Phe | Gly | Thr | Ile | |
| | | | 115 | | | | | 120 | | | | | 125 | | | |

| GCT | AAA | TAT | TTG | AAA | TCA | GAA | GGT | TTG | CTA | GCT | GAG | ACT | GGC | TAC | AAT | 551 |
|---|---|---|---|---|---|---|---|---|---|---|---|---|---|---|---|---|
| Ala | Lys | Tyr | Leu | Lys | Ser | Glu | Gly | Leu | Leu | Ala | Glu | Thr | Gly | Tyr | Asn | |
| | | 130 | | | | | 135 | | | | | 140 | | | | |

| CGT | TTG | ATG | ATT | GAA | AAG | CCT | TTT | GGT | ACA | TCA | TAC | GCC | ACC | GCA | GAA | 599 |
|---|---|---|---|---|---|---|---|---|---|---|---|---|---|---|---|---|
| Arg | Leu | Met | Ile | Glu | Lys | Pro | Phe | Gly | Thr | Ser | Tyr | Ala | Thr | Ala | Glu | |
| 145 | | | | | 150 | | | | | 155 | | | | | | |

| GAA | TTG | CAA | AGT | GAT | TTG | GAA | AAT | GCA | TTT | GAT | GAT | GAC | CAA | CTG | TTC | 647 |
|---|---|---|---|---|---|---|---|---|---|---|---|---|---|---|---|---|
| Glu | Leu | Gln | Ser | Asp | Leu | Glu | Asn | Ala | Phe | Asp | Asp | Asp | Gln | Leu | Phe | |
| 160 | | | | | 165 | | | | | 170 | | | | | 175 | |

| CGT | ATT | GAC | CAC | TAT | CTT | GGA | AAA | GAA | ATG | GTA | CAA | AAT | ATT | GCA | GCA | 695 |
|---|---|---|---|---|---|---|---|---|---|---|---|---|---|---|---|---|
| Arg | Ile | Asp | His | Tyr | Leu | Gly | Lys | Glu | Met | Val | Gln | Asn | Ile | Ala | Ala | |
| | | | | 180 | | | | | 185 | | | | | 190 | | |

| TTA | CGT | TTT | GGT | AAC | CCA | ATC | TTT | GAT | GCC | GCT | TGG | AAT | AAG | GAC | TAT | 743 |
|---|---|---|---|---|---|---|---|---|---|---|---|---|---|---|---|---|
| Leu | Arg | Phe | Gly | Asn | Pro | Ile | Phe | Asp | Ala | Ala | Trp | Asn | Lys | Asp | Tyr | |
| | | | 195 | | | | | 200 | | | | | 205 | | | |

| ATC | AAA | AAC | GTA | CAA | GTA | ACT | TTG | GCT | GAA | GTT | CTA | GGT | GTT | GAA | GAG | 791 |
|---|---|---|---|---|---|---|---|---|---|---|---|---|---|---|---|---|
| Ile | Lys | Asn | Val | Gln | Val | Thr | Leu | Ala | Glu | Val | Leu | Gly | Val | Glu | Glu | |
| | | 210 | | | | | 215 | | | | | 220 | | | | |

| CGT | GCT | GGT | TAC | TAC | GAT | ACC | ACT | GGC | GCC | CTT | TTG | GAT | ATG | ATT | CAA | 839 |
|---|---|---|---|---|---|---|---|---|---|---|---|---|---|---|---|---|
| Arg | Ala | Gly | Tyr | Tyr | Asp | Thr | Thr | Gly | Ala | Leu | Leu | Asp | Met | Ile | Gln | |
| 225 | | | | | 230 | | | | | 235 | | | | | | |

| AAC | CAC | ACA | ATG | CAA | ATT | GTT | GGT | TGG | TTA | GCA | ATG | GAA | AAA | CCT | GAA | 887 |
|---|---|---|---|---|---|---|---|---|---|---|---|---|---|---|---|---|
| Asn | His | Thr | Met | Gln | Ile | Val | Gly | Trp | Leu | Ala | Met | Glu | Lys | Pro | Glu | |
| 240 | | | | | 245 | | | | | 250 | | | | | 255 | |

| TCA | TTC | AAT | GAT | AAG | GAT | ATC | CGT | GCA | GCT | AAA | AAC | GCC | GCC | TTC | AAT | 935 |
|---|---|---|---|---|---|---|---|---|---|---|---|---|---|---|---|---|
| Ser | Phe | Asn | Asp | Lys | Asp | Ile | Arg | Ala | Ala | Lys | Asn | Ala | Ala | Phe | Asn | |
| | | | | 260 | | | | | 265 | | | | | 270 | | |

| GCA | TTA | AAG | ATT | TAT | AAC | GAA | GAA | GAA | GTG | AAT | AAG | TAC | TTC | GTT | CGT | 983 |
|---|---|---|---|---|---|---|---|---|---|---|---|---|---|---|---|---|
| Ala | Leu | Lys | Ile | Tyr | Asn | Glu | Glu | Glu | Val | Asn | Lys | Tyr | Phe | Val | Arg | |
| | | | 275 | | | | | 280 | | | | | 285 | | | |

| GCA | CAA | TAT | GGT | GCT | GGT | GAT | ACA | GCT | GAT | TAC | AAG | CCA | TAT | TTG | GAA | 1031 |
|---|---|---|---|---|---|---|---|---|---|---|---|---|---|---|---|---|
| Ala | Gln | Tyr | Gly | Ala | Gly | Asp | Thr | Ala | Asp | Tyr | Lys | Pro | Tyr | Leu | Glu | |
| | | 290 | | | | | 295 | | | | | 300 | | | | |

| | | | | | | | | | | | | | | | | |
|---|---|---|---|---|---|---|---|---|---|---|---|---|---|---|---|---|
| GAA | GCA | GAT | GTC | CCT | GCT | GAC | TCA | AAG | AAC | AAC | ACA | TTC | ATT | GCT | GGT | 1079 |
| Glu | Ala | Asp | Val | Pro | Ala | Asp | Ser | Lys | Asn | Asn | Thr | Phe | Ile | Ala | Gly | |
| | 305 | | | | 310 | | | | | 315 | | | | | | |
| GAA | TTG | CAG | TTC | GAT | TTG | CCA | CGT | TGG | GAA | GGT | GTT | CCT | TTC | TAT | GTT | 1127 |
| Glu | Leu | Gln | Phe | Asp | Leu | Pro | Arg | Trp | Glu | Gly | Val | Pro | Phe | Tyr | Val | |
| 320 | | | | | 325 | | | | | 330 | | | | | 335 | |
| CGT | TCA | GGT | AAG | CGT | TTG | GCT | GCC | AAG | CAA | ACA | CGT | GTT | GAT | ATT | GTA | 1175 |
| Arg | Ser | Gly | Lys | Arg | Leu | Ala | Ala | Lys | Gln | Thr | Arg | Val | Asp | Ile | Val | |
| | | | 340 | | | | | 345 | | | | | 350 | | | |
| TTT | AAG | GCT | GGC | ACA | TTC | AAC | TTT | GGT | TCA | GAA | CAA | GAA | GCA | CAA | GAA | 1223 |
| Phe | Lys | Ala | Gly | Thr | Phe | Asn | Phe | Gly | Ser | Glu | Gln | Glu | Ala | Gln | Glu | |
| | | | 355 | | | | | 360 | | | | | 365 | | | |
| TCA | GTA | CTC | TCA | ATC | ATC | ATT | GAT | CCA | AAG | GGT | GCT | ATT | GAA | TTG | AAG | 1271 |
| Ser | Val | Leu | Ser | Ile | Ile | Ile | Asp | Pro | Lys | Gly | Ala | Ile | Glu | Leu | Lys | |
| | | 370 | | | | | 375 | | | | | 380 | | | | |
| CTT | AAC | GCT | AAG | TCA | GTT | GAA | GAT | GCC | TTC | AAC | ACC | CGC | ACA | ATC | AAC | 1319 |
| Leu | Asn | Ala | Lys | Ser | Val | Glu | Asp | Ala | Phe | Asn | Thr | Arg | Thr | Ile | Asn | |
| 385 | | | | | 390 | | | | | 395 | | | | | | |
| TTG | GAT | TGG | GCA | GTA | TCT | GAT | GAA | GAC | AAG | AAG | AAC | ACA | CCA | GAA | CCA | 1367 |
| Leu | Asp | Trp | Ala | Val | Ser | Asp | Glu | Asp | Lys | Lys | Asn | Thr | Pro | Glu | Pro | |
| 400 | | | | | 405 | | | | | 410 | | | | | 415 | |
| TAC | GAA | CGT | ATG | ATT | CAC | GAT | ACA | ATG | AAT | GGT | GAC | GGA | TCA | AAC | TTT | 1415 |
| Tyr | Glu | Arg | Met | Ile | His | Asp | Thr | Met | Asn | Gly | Asp | Gly | Ser | Asn | Phe | |
| | | | | 420 | | | | | 425 | | | | | 430 | | |
| GCT | GAT | TGG | AAC | GGT | GTA | TCA | ATT | GCT | TGG | AAG | TTT | GTT | GAC | GCA | ATT | 1463 |
| Ala | Asp | Trp | Asn | Gly | Val | Ser | Ile | Ala | Trp | Lys | Phe | Val | Asp | Ala | Ile | |
| | | | 435 | | | | | 440 | | | | | 445 | | | |
| ACT | GCC | GTT | TAC | GAT | GCA | GAT | AAA | GCA | CCA | TTG | GAG | ACA | TAT | AAG | TCA | 1511 |
| Thr | Ala | Val | Tyr | Asp | Ala | Asp | Lys | Ala | Pro | Leu | Glu | Thr | Tyr | Lys | Ser | |
| | | 450 | | | | | 455 | | | | | 460 | | | | |
| GGT | TCA | ATG | GGT | CCT | GAA | GCA | TCA | GAC | AAG | CTA | TTA | GCT | GAA | AAT | GGC | 1559 |
| Gly | Ser | Met | Gly | Pro | Glu | Ala | Ser | Asp | Lys | Leu | Leu | Ala | Glu | Asn | Gly | |
| | 465 | | | | | 470 | | | | | 475 | | | | | |
| GAT | GCT | TGG | GTA | TTT | AAA | GGA | TAAGCACATT | TAAAAAGACC | ATCAAACAAA | | | | | | | 1610 |
| Asp | Ala | Trp | Val | Phe | Lys | Gly | | | | | | | | | | |
| 480 | | | | | 485 | | | | | | | | | | | |

TCTTTGTTTG ACGGTCTTTT TATATTGTCT GATTTAAGAT GCGTTTGGTT TCACGGAAAA 1670

CGGCTGACAA ATTGGTGTAT TGATCC 1696

(2) INFORMATION FOR SEQ ID NO:2:

(i) SEQUENCE CHARACTERISTICS:
        (A) LENGTH: 486 amino acids
        (B) TYPE: amino acid
        (D) TOPOLOGY: linear (ii) MOLECULE TYPE: protein (xi) SEQUENCE DESCRIPTION: SEQ ID NO:2:

| Met | Val | Ser | Glu | Ile | Lys | Thr | Leu | Val | Thr | Phe | Phe | Gly | Gly | Thr | Gly |
|---|---|---|---|---|---|---|---|---|---|---|---|---|---|---|---|
| 1 | | | | 5 | | | | | 10 | | | | | 15 | |
| Asp | Leu | Ala | Lys | Arg | Lys | Leu | Tyr | Pro | Ser | Val | Phe | Asn | Leu | Tyr | Lys |
| | | | 20 | | | | | 25 | | | | | 30 | | |
| Lys | Gly | Tyr | Leu | Gln | Glu | His | Phe | Ala | Ile | Val | Gly | Thr | Ala | Arg | Gln |
| | | | 35 | | | | | 40 | | | | | 45 | | |
| Gln | Leu | Ser | Asp | Asp | Glu | Phe | Lys | Gln | Leu | Val | Arg | Asp | Ser | Ile | Lys |
| | | 50 | | | | | 55 | | | | | 60 | | | |
| Asp | Phe | Thr | Glu | Asp | Gln | Ala | Gln | Ala | Glu | Ala | Phe | Ile | Ala | His | Phe |
| 65 | | | | | 70 | | | | | 75 | | | | | 80 |
| Ser | Tyr | Arg | Ala | His | Asp | Val | Thr | Asp | Ala | Ala | Ser | Tyr | Gly | Ile | Leu |
| | | | | 85 | | | | | 90 | | | | | 95 | |

| | | | | | | | | | | | | | |
|---|---|---|---|---|---|---|---|---|---|---|---|---|---|
| Lys | Ser | Ala | Ile<br>100 | Glu | Glu | Ala | Ala | Thr<br>105 | Lys | Phe | Asp | Ile<br>110 | Asp | Gly | Asn |
| Arg | Ile | Phe<br>115 | Tyr | Met | Ser | Val | Ala<br>120 | Pro | Arg | Phe | Phe<br>125 | Gly | Thr | Ile | Ala |
| Lys<br>130 | Tyr | Leu | Lys | Ser | Glu<br>135 | Gly | Leu | Leu | Ala | Glu<br>140 | Thr | Gly | Tyr | Asn | Arg |
| Leu<br>145 | Met | Ile | Glu | Lys | Pro<br>150 | Phe | Gly | Thr | Ser | Tyr<br>155 | Ala | Thr | Ala | Glu | Glu<br>160 |
| Leu | Gln | Ser | Asp | Leu<br>165 | Glu | Asn | Ala | Phe | Asp<br>170 | Asp | Gln | Leu | Phe<br>175 | Arg |
| Ile | Asp | His | Tyr<br>180 | Leu | Gly | Lys | Glu | Met<br>185 | Val | Gln | Asn | Ile | Ala<br>190 | Ala | Leu |
| Arg | Phe | Gly<br>195 | Asn | Pro | Ile | Phe | Asp<br>200 | Ala | Ala | Trp | Asn | Lys<br>205 | Asp | Tyr | Ile |
| Lys<br>210 | Asn | Val | Gln | Val | Thr<br>215 | Leu | Ala | Glu | Val | Leu<br>220 | Gly | Val | Glu | Glu | Arg |
| Ala<br>225 | Gly | Tyr | Tyr | Asp | Thr<br>230 | Thr | Gly | Ala | Leu | Leu<br>235 | Asp | Met | Ile | Gln | Asn<br>240 |
| His | Thr | Met | Gln | Ile<br>245 | Val | Gly | Trp | Leu | Ala<br>250 | Met | Glu | Lys | Pro<br>255 | Glu | Ser |
| Phe | Asn | Asp | Lys<br>260 | Asp | Ile | Arg | Ala | Ala<br>265 | Lys | Asn | Ala | Ala | Phe<br>270 | Asn | Ala |
| Leu | Lys | Ile<br>275 | Tyr | Asn | Glu | Glu | Glu<br>280 | Val | Asn | Lys | Tyr | Phe<br>285 | Val | Arg | Ala |
| Gln | Tyr<br>290 | Gly | Ala | Gly | Asp | Thr<br>295 | Ala | Asp | Tyr | Lys | Pro<br>300 | Tyr | Leu | Glu | Glu |
| Ala<br>305 | Asp | Val | Pro | Ala | Asp<br>310 | Ser | Lys | Asn | Asn | Thr<br>315 | Phe | Ile | Ala | Gly | Glu<br>320 |
| Leu | Gln | Phe | Asp | Leu<br>325 | Pro | Arg | Trp | Glu | Gly<br>330 | Val | Pro | Phe | Tyr | Val<br>335 | Arg |
| Ser | Gly | Lys | Arg<br>340 | Leu | Ala | Ala | Lys | Gln<br>345 | Thr | Arg | Val | Asp | Ile<br>350 | Val | Phe |
| Lys | Ala | Gly<br>355 | Thr | Phe | Asn | Phe | Gly<br>360 | Ser | Glu | Gln | Glu | Ala<br>365 | Gln | Glu | Ser |
| Val | Leu<br>370 | Ser | Ile | Ile | Ile | Asp<br>375 | Pro | Lys | Gly | Ala | Ile<br>380 | Glu | Leu | Lys | Leu |
| Asn<br>385 | Ala | Lys | Ser | Val | Glu<br>390 | Asp | Ala | Phe | Asn | Thr<br>395 | Arg | Thr | Ile | Asn | Leu<br>400 |
| Asp | Trp | Ala | Val | Ser<br>405 | Asp | Glu | Asp | Lys | Lys<br>410 | Asn | Thr | Pro | Glu | Pro<br>415 | Tyr |
| Glu | Arg | Met | Ile<br>420 | His | Asp | Thr | Met | Asn<br>425 | Gly | Asp | Gly | Ser | Asn<br>430 | Phe | Ala |
| Asp | Trp | Asn<br>435 | Gly | Val | Ser | Ile | Ala<br>440 | Trp | Lys | Phe | Val | Asp<br>445 | Ala | Ile | Thr |
| Ala | Val<br>450 | Tyr | Asp | Ala | Asp | Lys<br>455 | Ala | Pro | Leu | Glu | Thr<br>460 | Tyr | Lys | Ser | Gly |
| Ser<br>465 | Met | Gly | Pro | Glu | Ala<br>470 | Ser | Asp | Lys | Leu | Leu<br>475 | Ala | Glu | Asn | Gly | Asp<br>480 |
| Ala | Trp | Val | Phe | Lys<br>485 | Gly |

( 2 ) INFORMATION FOR SEQ ID NO:3:

( i ) SEQUENCE CHARACTERISTICS:
        ( A ) LENGTH: 72 base pairs
        ( B ) TYPE: nucleic acid
        ( C ) STRANDEDNESS: single ( D ) TOPOLOGY: linear ( x i ) SEQUENCE DESCRIPTION: SEQ ID NO:3:

RTTTTGAACC ATTTCTTTWC CTAAATAATG ATCAATWCKA AATAATTGRT TATCATCAAA  60

AGCGTTTTCA AA  72

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Phe Leu Leu Lys Ser Pro Ser Tyr Asp Lys
1               5                   10

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Phe Leu Leu Lys Ser Pro Ser Tyr Val Lys
1               5                   10

CLONING AND OVEREXPRESSION OF GLUCOSE-6-PHOSPHATE DEHYDROGENASE FROM LEUCONOSTOC DEXTRANICUS

Glucose-6-phosphate dehydrogenase (G6P-DH) catalyzes the first step in the oxidative metabolism of glucose. In this process glucose-6-phosphate is oxidized to gluconic acid-6-phosphate while $NAD^+$ or/and $NADP^+$ is reduced as the cosubstrate. The oxidation of glucose ultimately results in the production of pentose sugars for the nucleic acid metabolism.

Glucose-6-phosphate dehydrogenase can for example be isolated from *Leuconostoc mesenteroides*. This enzyme can use $NAD^+$ as well as $NADP^+$ as cofactor, in contrast to the enzyme from yeast which is specific for $NADP^+$. The enzyme is present as a dimer consisting of two identical monomeric subunits with a molecular weight of 55000 D. Its specific activity at 25° C. is 550 U/mg.

Disadvantages of the process for isolating G6P-DH from bacteria of the genus Leuconostoc are inter alia that the lactic acid bacteria have complex nutrient requirements and therefore grow only slowly in those nutrient media used on a large technical scale and only reach a low cell density. In addition the content of G6P-DH in the biomass is only very low when using Leuconostoc (about 1% of the total cell protein). Thus, large fermentation dimensions are necessary in order to provide adequate amounts of G6P-DH. Moreover, it is only possible to obtain an enzyme preparation with a low specific activity because of the large amounts of foreign protein.

The most important disadvantage of the known G6P-DH from Leuconostoc bacteria is, however, their low temperature stability.

The object of the present invention was therefore to provide a glucose-6-phosphate dehydrogenase which no longer has the disadvantages of the state of the art.

The object according to the present invention is achieved by the provision of a glucose 6-phosphate dehydrogenase which contains the amino acid sequence shown in SEQ ID NO:1 and is obtainable from *Leuconostoc mesenteroides*, subspecies dextranicus (DSM 20187) which is denoted *Leuconostoc dextranicus* in the following.

In addition the present invention also provides a DNA which contains a sequence encoding the enzyme according to the present invention shown in SEQ ID NO:1 or a corresponding sequence within the scope of the degeneracy of the genetic code.

The recombinant DNA according to the present invention was isolated by screening a *L. dextranicus* (DSM 20187) gene bank with a suitable oligonucleotide probe which is described below in more detail.

When the recombinant DNA according to the present invention is expressed in *E. coli* cells it surprisingly turned out that even small fermentation volumes are sufficient to provide the desired amount of enzyme. Compared to the isolation of G6P-DH from Leuconostoc, a reduction in the fermentation volume by a factor 1:500 to 1:1000 is achieved. Moreover, G6P-DH preparations are obtained in high purity, i.e. with a specific activity of ca. 900 U/mg, with a less extensive purification procedure. However, a surprisingly special characteristic of the recombinant enzyme according to the present invention is a substantially improved temperature stability compared to the known enzyme when isolated from *E. coli*. An additional advantage of the recombinant enzyme in contrast to the known enzyme from Leuconostoc is that it does not react with glucose. This well-known unspecific reaction of the Leuconostoc enzyme with glucose (Olive and Levy, Biochemistry 6 (1967), 730) has previously been a major drawback in carrying out enzyme tests since this could lead to false results in determinations because of the presence of glucose in blood, serum or plasma. Finally the recombinant enzyme also differs from the known G6P-DH in that the $K_m$ value for $NADP^+$ is different and the effect of activators and inhibitors (e.g. phosphate, glycerol, magnesium ions, hydrogen carbonate) is different.

The present invention also provides a recombinant vector which contains one or several copies of the recombinant DNA according to the present invention. Such a vector is intended to enable the expression of the recombinant DNA according to the present invention in foreign host organisms. The vector according to the present invention can be a vector which integrates into the chromosomal DNA of the host cell (e.g. bacteriophage lambda), it can, however, also be present extrachromosomally in the host cell (plasmid). The vector according to the present invention is preferably a plasmid.

The vector according to the present invention can be a eukaryotic as well as a prokaryotic vector, it is, however, preferably a prokaryotic vector, i.e. it is suitable for multiplication in prokaryotic host organisms. The recombinant vector has particularly preferably an origin of replication which is active in *E. coli* i.e. it can be multiplied in *E. coli*.

In a particularly preferred embodiment the recombinant vector according to the present invention contains the nucleic acid sequence coding for the glucose-6-phosphate dehydrogenase which is under the control of a promoter sequence from Leuconostoc dextranicus which functions in *E. coli* and which is included in the first 122 nucleotides (upstream of the G6P-DH gene) of the nucleic acid sequence shown in SEQ ID NO:1.

In order to exhibit promoter properties it is not necessary that the DNA region has exactly this sequence of 122 nucleotides. Derived sequences or fragments of this sequence which have promoter properties are also suitable. Under a derived biologically active sequence in the sense of the invention it is therefore understood that individual nucleotides or short nucleotide sequences from the promoter sequence can be deleted, substituted or inserted and namely in such a way that the promoter activity of the sequence is preserved. A person skilled in the art does indeed know that for a promoter it is not necessary to conserve the whole sequence but rather only particular partial regions. In prokaryotic promoter sequences these are in particular the regions at −35 and at −10 with respect to the transcription start.

Thus the invention also includes a recombinant DNA which has the first 122 nucleotides of the nucleic acid sequence shown in SEQ ID NO:1 or a sequence derived therefrom with promoter properties. Surprisingly this Leuconostoc promoter also results in a good protein expression in *E. coli*. Thus, this promoter can also be used for the expression of heterologous genes, i.e. genes which are different from the G6P-DH gene, in gram-negative bacteria, preferably *E. coli* bacteria.

The present invention in addition provides a microorganism which is transformed with a recombinant vector according to the present invention. In this connection it is preferably a gram-negative bacterium, particularly preferably an *E. coli* bacterium.

The recombinant DNA according to the present invention can be obtained by (1) isolating chromosomal *Leuconostoc dextranicus* DNA and cleaving it with a suitable restriction enzyme, (2) incorporating the cleaved *L. dextranicus* DNA into a vector, transforming a suitable organism with the vector and producing a gene bank in this way, (3) screening the gene bank from step (2) with a nucleic acid probe which has a sequence which is specific for the glucose-6-phosphate dehydrogenase gene whereby these probes are constructed in lactic acid bacteria with respect to the codon usage and (4) analyzing the clones of the gene bank which react positively with the probe from step (3).

The chromosomal *L. dextranicus* (DSM 20187) DNA can be isolated by combined polyethylene glycol/lysozyme treatment and subsequent incubation with proteinase K. The cleavage of the isolated *L. dextranicus* DNA with a suitable restriction enzyme, the ligation of the cleaved DNA into a suitable cloning vector and the transformation of a suitable organism with the recombinant cloning vector for the production of a gene bank can be carried out in a manner familiar to one skilled in the area of molecular biology. The next step is the examination of the gene bank produced in this way with a nucleic acid probe which has a sequence specific for the glucose-6-phosphate dehydrogenase gene.

A peptide sequence of G6-PDH from L. mesenteroides with a lysine residue (*) which can be pyridoxylated is known from Haghighi et al., Biochemistry 21 (1982), 6415–6420. This sequence is as follows: Phe-Leu-Leu-Lys*-Ser-Pro-Ser-Tyr-(Asp/Val)-Lys (SEQ ID NO: 4 and SEQ ID NO:5. However, it was not possible to derive an oligonucleotide probe from this sequence which can be used to find a hybridization signal in the *L. dextranicus* gene bank. *

1) Olive and Levy, Biochem. 6 (1967), 730 *
2) DeMoss, in Methods in Enzymology, Vol 1., p. 328, Acad. Press, New York, 1955 *
3) Levy, 626th Meeting Sheffield, p. 13 (1988) *
4) Concentration 0.15 mol/l *
5) Arch. Biochem. and Biophys. 149 (1972), 102–109

Bhadbhade et al., FEBS Letters 211 (1987), 243–246 discloses a peptide sequence from the active centre of the G6P-DH from L. mesenteroides with a high homology to human G6P-DH. The oligonucleotide probe mentioned in Example 2 with a length of 72 bases (SEQ ID NO:3) was produced from the multitude of oligonucleotide probes which can be constructed from this peptide sequence.

Screening the *L. dextranicus* DNA gene bank with this oligonucleotide in a 5' end-labelled form finally produced a positive clone which allowed the determination of the sequence of the *L. dextranicus* G6P-DH gene.

The DNA sequence of the G6P-DH gene from *L. dextranicus* was determined according to the method of Sanger. It is shown in SEQ ID NO:1.

SEQ ID NO:1 also shows the amino acid sequence of the G6P-DH from L. dextranicus which was determined from it. From this it can be seen that the amino acid sequence of the enzyme according to the present invention does not correspond to the sequence of the L. mesenteroides enzyme described in FEBS Letters 211 (1987), 243–246 in 6 out of 42 positions.

In addition the invention includes a process for the production of a G6P-DH with the amino acid sequence shown in SEQ ID NO:1 in which (1) a suitable host organism is transformed with a DNA or a vector according to the present invention which contains one or several copies of this DNA, (2) the transformed host organism is cultured in a suitable medium and (3) the protein is isolated from the medium or the cells.

The expression of the recombinant protein according to the present invention in a transformed host organism, preferably in a prokaryotic host organism, particularly preferably in an *E. coli* cell, is in principle possible under the control of any suitable promoter. Thus, in *E. coli* an expression of the G6P-DH is e.g. possible under the control of heterologous promoters such as e.g. the tac promoter, mgl promoter or pfl promoter. However, the expression is preferably carried out constitutively under the control of a Leuconostoc promoter, particularly preferably under the control of the promoter sequence shown in SEQ ID NO:1 or of a promoter sequence derived therefrom (corresponding to the first 122 nucleotides of SEQ ID NO:1). The plasmid pUC G6P-DH 1.8 which is shown in FIG. 1 is most preferred.

The commercially available *E. coli* strain HB 101 was chosen as a suitable *E. coli* host strain. When transforming *E. coli* HB 101 with pUC G6P-DH 1.8 it was found that the plasmid has a high stability in the cell and the expression of the G6P-DH can be carried out over several passages even without selection pressure.

It is intended to elucidate the present invention by the following examples in conjunction with SEQ ID NO:1 and 3 as well as FIG. 1.

SEQ ID NO:1 shows the nucleotide sequence of the Leuconostoc DNA insertion in pUC G6P-DH 1.8 in which the first 122 bases upstream of the coding region for the L. dextranicus G6P-DH promoter and the bases 123–1580 represent the nucleotide sequence of the L. dextranicus G6P-DH gene which codes for a protein with the amino acid sequence which is also shown, SEQ ID NO:2 shows the oligonucleotide probe for the part of the G6P-DH gene from *Leuconostoc mesenteroides* which codes for a region of the active centre of the G6P-DH of *L. mesenteroides* which has a high homology to human G6P-DH.

FIG. 1 shows the plasmid pUC-G6P-DH 1.8.

EXAMPLE 1

Isolation of Chromosomal DNA from *Leuconostoc dextranicus*

Genomic DNA is isolated from *Leuconostoc dextranicus* according to the following method:

*Leuconostoc dextranicus* (DSM 20187) is cultured at 30° C. in APT medium (Merck No. 10454). The cells from 100 ml culture broth are centrifuged down, washed in 10 ml 20 mmol/l Tris/HCl pH 8.0 and finally resuspended in 15 ml of this buffer solution. After addition of 5 ml 24% (w/v) polyethylene glycol 6000 and 20 mg lysozyme it is incubated for 16 h at 4° C. The cell lysis is carried out by addition of 1 ml 20 % (w/v) SDS. 2 mg protease K are added and incubated for 60 min at 37° C. The further purification of the DNA is carried out by sequential phenol and chloroform extraction, treatment with RNAse A (0.5 mg/60 min at 37° C.), renewed phenol and chloroform extraction and a final ethanol precipitation.

EXAMPLE 2

Edtermination of the Size of Genomic DNA Fragments Which Code for G6P-DH

The oligonucleotide shown in SEQ ID NO:3 is used for the hybridization.

5 μg aliquots of genomic DNA from *L. dextranicus* are cleaved with different restriction endonucleases (BclI, ClaI, HindIII, PstI, XbaI), electrophoretically separated on a 0.8% agarose gel and subsequently transferred onto a nitrocellulose filter. After prehybridization with a solution of 6 x SSC buffer, 0.7% skim milk, such a filter is incubated overnight in the same solution at 40° C. which additionally contains the above nucleotide which is radioactively end-labelled with $^{32}P$. After washing, drying and autoradiography, it can be established that a DNA fragment of ca. 3.4 kb size produced by the restriction enzyme BclI hybridizes with the oligonucleotide.

EXAMPLE 3

Cloning of a DNA Fragment Which Codes for G6P-DH

20 μg genomic DNA from *L. dextranicus* is cleaved with BclI and is fractionated in a gel of low-melting agarose. DNA fragments with a size of ca. 3.4 kb+/−0.2 kb are cut out of the gel. This gel piece is equilibrated with ligase buffer (Maniatis et al., 1982, Molecular Cloning, p 474) and liquified at 65° C. Afterwards 0.1 μg pUC18 DNA is cleaved with BamHI and 5 U T4 ligase are added, incubated for 10 min at 37° C. and then for 16 h at 15° C. The restriction endonuclease BamHI produces protruding DNA ends which are compatible with the ends produced by BclI.

Cells of *E. coli* HB 101 (DSM 1607) are cultured in 20 ml nutrient medium and converted into a competent state by calcium chloride treatment (Maniatis et al. 1982, Molecular Cloning, pp. 250–252). The ligation preparation obtained above is liquified again for 5 min at 65° C. after addition of one volume portion of 50 mmol/l Tris/HCl pH 7.5 and is used for the transformation. The cells treated in this way are plated on LB agar plates with 50 μg/ml ampicillin and incubated at 37° C. for one day.

The fully grown colonies are transferred onto new LB agar plates with 50 μl ampicillin onto which nitrocellulose filters are placed. After the colonies are again fully grown, the filters are lifted, the colonies are lysed as described by Grunstein and Hogness Proc. Natl. Acad. Sci. USA, 72 (1975) 3961 and hybridized with the radioactively labelled oligonucleotide probe described under 2. After autoradiography clones with recombinant, G6P-DH coding plasmids can be identified and isolated from the original plates. After isolation and characterization of the plasmid DNA of such clones it turns out that these have a size of ca. 6 kb. This means that a DNA fragment of ca. 3.4 kb size is inserted into the pUC18 DNA. Such a recombinant plasmid is chosen for the further processing.

EXAMPLE 4

Resection and Expression of the Gene

The recombinant plasmid obtained above can be cut up into a fragment of ca. 2.2 kb and one of ca. 3.8 kb size by cleavage with the restriction enzymes XbaI and SpeI. This 3.8 kb fragment now only contains DNA sequences from pUC18 and the nucleotide sequence of SEQ ID NO:1. Isolation and religation of the 3.8 kb fragment and subsequent transformation in *E. coli* HB 101 leads to a clone which expresses the G6P-DH gene. The G6P-DH gene is subcloned in this positive clone as a 1.8 kb fragment (SpeI/KpnI) in a commercial pUC18 vector cleaved with XbaI and KpnI in the polylinker region whereby the KpnI cleavage site originates from the vector portion of the positive clone from the gene bank. Thus a SpeI/BclI fragment from the Leuconostoc dextranicus genome is present. The DNA sequence of the complete subcloned 1.8 kb SpeI/BclI fragment is shown in SEQ ID NO:1.

The resulting recombinant plasmid contains the G6P-DH gene under the control of its own Leuconostoc promoter. It was denoted pUC-G6P-DH 1.8 and is shown in FIG. 1.

The expression direction of the G6P-DH gene in this case is in the opposite direction to the lac promoter (pLAC) on pUC18.

In order to determine the enzyme activity and purify the G6P-DH, such a clone is inoculated in a test tube with 5 ml LB nutrient medium containing 50 μg/ml ampicillin and is grown overnight at 37° C. An Erlenmeyer flask containing 1 l LB nutrient medium with 50 μg/ml ampicillin is inoculated with this culture and incubated again overnight at 37° C. while shaking. The cells are harvested by centrifugation.

EXAMPLE 5

Concentration and Characterization of Recombinant G6P-DH from *E. coli*

5.1 Concentration Procedure

1. Lysis

Suspend 5 kg biomass (*E. coli* HB101 pUC-G6P-DH 1.8) in 25 l potassium phosphate buffer 10 mmol/l, pH 7.5 containing $10^{-3}$ mol/l $MgCl_2$ and lyse the cells with an APV-Gaulin high pressure homogenizer at 800 bar homogenization pressure.

Cool the resulting suspension to +4° C. and centrifuge.

2. Ammonium sulphate fractionation

Add solid ammonium sulphate to the crude extract up to a concentration of 1.9 mol/l and centrifuge down the precipitated precipitate. Precipitate the supernatant further with ammonium sulphate up to a concentration of 3.0 mol/l and centrifuge down the precipitate.

3. Heating

Dissolve the second ammonium sulphate precipitate with 20 mmol/l potassium phosphate buffer, pH 6.0 containing 1 mmol/l EDTA and heat for 20 min to 52° C. Centrifuge down the precipitated precipitate.

4. First crystallization

Add solid ammonium sulphate slowly to the supernatant from 3. to a concentration of 2.1 mol/l; adjust the pH with NaOH to 6.0. The G6P-DH crystallizes out overnight. The crystallization should be carried out at room temperature and while stirring gently. Centrifuge down the enzyme crystals.

5. Second crystallization

Dissolve the precipitate with 20 mmol/l potassium phosphate buffer, pH 6.0 containing 1 mmol/l EDTA and add solid ammonium sulphate to 1.9 mol/l. Adjust the pH again to 6.0 and allow the enzyme to crystallize out overnight at room temperature and while stirring gently.

6. Dialysis

Centrifuge down the enzyme crystallizate and dissolve the precipitate in a concentrated form with 10 mmol/l potassium phosphate buffer, pH 6.0 containing 1 mmol/l EDTA and dialyse for 24 hours against the same buffer.

7. Lyophilization

Lyophilize the enzyme solution without additives. This results in ca. 210 g lyophilizate with ca. 900 U/mg activity.

5.2 Characterization of Recombinant G6P-DH

The G6P-DH produced by genetic engineering differs in its properties from the known enzyme from Leuconostoc.

The disadvantages of the known Leuconostoc enzyme are as follows:

The long-term stability is low. In addition the enzyme converts glucose which can lead to false results when measuring in blood, serum or plasma since glucose is always present in such samples. The lack of specificity of G6P-DH is described in Archives of Biochemistry and Biophysics 149 (1972) 102–109.

The differentiating features are:

1. $K_m$ NADP (in 0.1 mol/l Tris pH 7.8; 25° C.

| rec G6P-DH | G6P-DH from Leuconostoc |
|---|---|
| $3.7 \times 10^{-5}$ | $7.4 \times 10^{-6}$ mol/l[1] |
| | $5.7 \times 10^{-6}$ mol/l[3] |
| | $9.9 \times 10^{-6}$ mol/l[2] |

2. Effect of Activators/Inhibitors

| | rel. activity (with respect to activity without additive) | | | |
|---|---|---|---|---|
| | rec.G6P-DH cosubstrate | | G6P-DH from Leuconostoc cosubstrate | |
| Addition of | NAD+ | NADP+ | NAD+ | NADP+ |
| 5 mmol/l phosphate | 100% | 80% | activation[2] | |
| 50 mmol/l phosphate | 100% | 80% | 107%[1] | 118%[1] |
| 30% glycerol | 60% | 30% | 30%[1] | 30%[1] |
| 30 mmol/l Mg$^{2+}$ | 100% | 100% | 80%[1] | 80%[1] |
| 0.3 mol/l hydrogen carbonate | 100% | 100% | 120%[1] | 120%[1] |

3. Specificity

| Specificity for | rec G6P-DH with NAD(P)+ | G6P-DH from Leuconostoc |
|---|---|---|
| glucose[4] | no conversion | conversion[5] |
| 2-deoxy-glucose-6P[4] | 5% | no conversion |

4. Temperature Stability

| Temperature | rel. activity rec. G6P-DH | (with reference to 20° C.) G6P-DH from Leuconostoc dextranicus produced according to[1] |
|---|---|---|
| 40° C. | 100% | 100% |
| 50° C. | 100% | 97% |
| 60° C. | 100% | 90% |
| 70° C. | 43% | 4% |

The determination of the temperature stability was carried out in 3.2 mol/l ammonium sulphate pH 6.0 for 10 minutes. (Initial activity of the enzyme 2500 U/ml).

The determination of activity and specificity was carried out as described in Example 6.

EXAMPLE 6

Determination of the Activity of Glucose-6-Phosphate-Dehydrogenase

G6P-DH converts glucose-6-phosphate and NAD+ to gluconate-6-phosphate and NADH. The NADH formed is measured photometrically at 340 nm.

0.05 ml sample (G6P-DH, volume activity should if possible be between 0.3 and 0.5 U/ml) is added to 3 ml of a reagent consisting of Tris buffer (0.1 mol/l pH 7.8, 3 mmol/l MgCl$_2$), 0.1 mmol/l NAD+, free acid and 0.15 mol/l glucose-6-phosphate at 25° C. and the increase in absorbance ($\Delta A$/min) is monitored. The volume activity is calculated as follows:

$$\text{Volume activity} = \frac{3.05}{\epsilon \times 1 \times 0.05} \times \Delta A \text{ min}[U/\text{ml}]$$

$$\epsilon_{340} = 6.3[\text{mmol}^{-1} \times 1 \times \text{cm}^{-1}]$$

---

We claim:

1. Isolated and purified glucose-6-phosphate dehydrogenase consisting essentially of the amino acid sequence shown in SEQ ID NO: 1.

* * * * *